United States Patent
Hill et al.

(10) Patent No.: US 7,402,722 B2
(45) Date of Patent: Jul. 22, 2008

(54) ABSORBENT ARTICLE

(75) Inventors: Donna Rene Hill, Verona, KY (US); Thomas Ward Osborn, III, Clifton, OH (US); Catherine Cornick Davis, Sharonville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/725,462

(22) Filed: Mar. 19, 2007

(65) Prior Publication Data

US 2007/0232167 A1 Oct. 4, 2007

Related U.S. Application Data

(63) Continuation of application No. 10/744,361, filed on Dec. 22, 2003, now abandoned, which is a continuation of application No. PCT/US02/20617, filed on Jun. 28, 2002.

(60) Provisional application No. 60/302,507, filed on Jun. 29, 2001.

(51) Int. Cl.
*B32B 27/12* (2006.01)
*A61F 13/15* (2006.01)
*A61F 13/20* (2006.01)

(52) U.S. Cl. .................. 604/360; 442/123; 604/358; 604/359; 604/374

(58) Field of Classification Search ............ 442/123; 604/358–360
See application file for complete search history.

(56) References Cited

U.S. PATENT DOCUMENTS

| 4,722,937 | A | 2/1988 | Jacob |
| 5,290,894 | A * | 3/1994 | Melrose et al. ............. 526/315 |
| 5,753,252 | A | 5/1998 | Brown-Skrobot |
| 5,811,471 | A | 9/1998 | Shanbrom |
| 6,150,146 | A | 11/2000 | Hamade et al. |
| 2006/0252691 | A1 | 11/2006 | Balaban |

FOREIGN PATENT DOCUMENTS

| CA | 1123155 | 5/1982 |
| CA | 1 192 701 | 9/1985 |
| EP | 0 483 812 A1 | 5/1992 |
| EP | 1 103 275 A1 | 5/2001 |
| WO | WO 01/26647 A1 | 4/2001 |

OTHER PUBLICATIONS

Kass, "Interaction of Magnesium Ion, Oxygen Tension, and Temperature in the Production of Toxic-Shock-Syndrome Toxin-1 by *Staphylococcus aureus*", The Journal of Infectious Diseases, vol. 155, No. 4, Apr. 1987, pp. 812-815.

* cited by examiner

*Primary Examiner*—Lynda Salvatore
(74) *Attorney, Agent, or Firm*—Gary J. Foose; David M. Weirich; Ken K. Patel

(57) ABSTRACT

An absorbent article has an absorbent material and an outer surface including an inhibitor which is partially bound to the absorbent material and substantially inhibits the colonization of bacteria within the absorbent article.

An absorbent article has an absorbent material. The absorbent material has an outer surface. The absorbent article includes a pre-toxin limiting agent which is partially bound to the absorbent material and substantially retards the production of bacteria-produced toxins by the bacteria residing within the absorbent article.

An absorbent article has an absorbent material. The absorbent material has an outer surface. The absorbent article includes a toxin enclosing agent. The toxin enclosing agent substantially inhibits the migration of toxin outwardly from within the absorbent article towards the outer surface of the absorbent article.

19 Claims, 4 Drawing Sheets

Fig. 3A Effects of Temperature on Toxin Production of Staph. aureus
Journal of Infectious Disease Apr 1987
;155(4):812-814 Kass, Kendrick, Tai, Parsonnet

ABSORBENT ARTICLE

CROSS REFERENCE TO RELATED APPLICATION

This application is a continuation application of prior U.S. application Ser. No. 10/744,361, filed Dec. 22, 2003 now abandoned, which is a continuation application of prior copending International Application No. PCT/US02/20617, filed Jun. 28, 2002, designating the U.S., which claims the benefit of U.S. Provisional Application No. 60/302,507, filed Jun. 29, 2001.

FIELD OF INVENTION

The present invention relates to a tampon which employs mechanisms to reduce the potential risk of Toxic Shock Syndrome ("TSS") associated with tampon wear or any other absorptive product such as surgical gauze or any product whose use has been directly associated with toxic shock syndrome, such as but not excluded to diaphragms and cervical cups.

BACKGROUND OF THE INVENTION

Disposable absorbent devices for the absorption of human exudates are widely used. These disposable devices typically have a compressed mass of absorbent formed in the desired shape, which is typically dictated by the intended consumer use. For example, in the case of menstrual tampons, the device is intended to be inserted at least partially into a body cavity for absorption of the body fluids generally discharged during a woman's menstrual period.

There exists in the human female body a complex process which maintains the vagina and physiologically related areas in a healthy state. In females between the age of menarche and menopause, the normal vagina provides an ecosystem for a variety of microorganisms, which must be maintained in a relatively delicate balance. Bacteria are the predominate type of microorganisms present in the vagina, and most women harbor about $10^9$ bacteria per gram of vaginal secretions. The bacterial flora of the vagina is comprised of both aerobic and anaerobic bacteria. The more commonly isolated bacteria include *Lactobacillus* species, *Corynebacteria* species, *Gardnerella vaginalis, Staphylococcus* species, *Peptococcus* species, aerobic and anaerobic *Streptococcal* species, and *Bacteroides/Preuotella* species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (Herpes simplex). These latter organisms are generally associated with vaginitis or sexually transmitted diseases, although they may be present in low numbers without causing symptoms.

Physiological, social and idiosyncratic factors affect the quantity and species of bacteria present in the vagina. Physiological factors include age, days of the menstrual cycle, and pregnancy. For example, vaginal flora present in the vagina throughout the menstrual cycle can include *Lactobacilli, corynebacterium, ureaplasma,* and *mycoplasma*. Social and idiosyncratic factors include presence and method of birth control, sexual practices, systemic disease (e.g., diabetes), and medication.

Bacterial proteins and metabolic products produced in the vagina can affect other microorganisms and the human host. For example, generally the pH of the vagina between menstrual periods is mildly acidic, having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and making the vagina inhospitable to some species of bacteria such as *S. aureus*. The low pH is a consequence of the growth of *Lactobacilli* and their production of acidic products. Microorganisms in the vagina can also produce antimicrobial compounds such as hydrogen peroxide and bacteriocins which attack and eliminate other bacterial species. One example is the lactocins, bacteriocin-like products of *Lactobacilli* directed against other species of *Lactobacilli*. Some microbial products may affect the human host. For example, *S. aureus* can produce and excrete into its environment a variety of exoproteins including enterotoxins, toxic shock syndrome toxin-1 ("TSST-1"), and enzymes such as protease and lipase.

Vaginal menstrual toxic shock syndrome is a rare syndrome characterized by rapid onset of high fever, vomiting, diarrhea, and rash followed by a rapid drop in blood pressure and vital organ failure. TSS is associated with the presence of *S. aureus* bacteria and one or more exotoxins which are produced by the bacteria. The exotoxins associated with TSS include but may not be limited to *Streptococcus*: Exotoxin A, Exotoxin B, Exotoxin C and Staphylococca: Pyrogenic Exotoxin C, Enterotoxin A, Enterotoxin B, Enterotoxin C, Enterotoxin F, and TSST-1. Using traditional culture based techniques, *S. aureus* has been identified in the vagina of approximately 16% of healthy women of menstrual age (Recent clinical studies using DNA based techniques have shown this number to be much higher). It has been found that approximately 10% of the *S. aureus* isolated from the vagina are capable of producing TSST-1. TSS is not caused by the bacteria per se but rather by the toxic effects of the associated exotoxin which can pass from the vagina and other internal body cavities into the blood stream.

TSS has been associated with the use of absorbent pads within the vagina which may promote the growth of bacteria and the production of exotoxin in their vicinity. The syndrome has been observed with surgical dressings, and is also associated with the use of catamenial tampons. The syndrome appears to occur with elevated frequency in association with those absorbent pads which are characterized by high levels of absorbency and which accordingly are left inside the body for extended periods.

While a preferred approach for reducing the risk of TSS when using absorbent pads is proper use and frequent changes of new pads for used ones, various other approaches have been proposed by the art for reducing the risk of TSS associated with an internal absorbent pad. One approach is the incorporation of antimicrobial or bacteriocidal agents into the absorbent pad such as the use of iodine bactericides in tampons and catamenial sponges. Such an approach is not always suitable for use in the catamenial product, however, because a bactericide which is active against *S. aureus* can adversely affect other beneficial bacteria which make up the vaginal flora, thereby upsetting the healthy balance discussed above. Another related method describes the use of catamenial tampons comprising substances such as organic acids which will maintain a pH of about 4.5 to about 2.5 in the fluids absorbed during the use of the tampon such that the growth of pathogenic bacteria is inhibited.

Other approaches are directed to inactivation of the TSS toxin such as the administration of L-ascorbic acid for the detoxification of the *S. aureus* toxins, Pyrogenic, Exotoxin C (Schlievert) and Staphylococcal Enterotoxin F (Bergdoll)

TSS-1. While this method does not ascribe a mechanism for the effectiveness of ascorbic acid at neutralizing TSS-1, it observes that L-ascorbic acid is known to be a reducing agent and strong antioxidant and that it may operate to inactivate bacterial toxins by reducing disulfide bonds within the toxins.

Another approach is directed to the incorporation of substances within an absorbent pad which inhibit the production of TSS exotoxins by *S. aureus*. This method describes the incorporation of non-toxic divalent magnesium cations in absorbent pads to reduce the concentrations of available magnesium binding ions below those critical for optimal production of TSST-1 and other *staphylococcus* products.

Despite these developments, there remains a desire in the art for absorbent pads suitable for internal use, including catamenial tampons, which are characterized by improved immobilization of TSST-1 toxin generated within the absorbent product without adversely affecting the normal vaginal flora.

SUMMARY OF THE INVENTION

The present invention encompasses an absorbent article having an absorbent material and an outer surface including an inhibitor which is at least partially bound to the absorbent material and substantially inhibits the colonization of bacteria within the absorbent article.

The present invention can also encompass an absorbent article having an absorbent material. The absorbent material has an outer surface. The absorbent article includes a pre-toxin limiting agent which is at least partially bound to the absorbent material and that substantially retards the production of bacteria-produced toxins by the bacteria residing within the absorbent article.

In another embodiment, an absorbent article has an absorbent material. The absorbent material has an outer surface. The absorbent article includes a pre-toxin limiting agent which is at least partially bound to the absorbent material and a pre-toxin limiting agent that substantially de-activates bacteria produced toxins arising from bacteria residing within the absorbent article.

In yet another embodiment, an absorbent article has an absorbent material. The absorbent material has an outer surface. The absorbent article includes a toxin enclosing agent. The toxin enclosing agent substantially inhibits the migration of toxin outwardly from within the absorbent article towards the outer surface of the absorbent article.

In another aspect, an absorbent article has an absorbent material. The absorbent material has an outer surface. The absorbent article includes a temperature limiting agent. The temperature limiting agent substantially inhibits the elevation of temperatures within the absorbent article.

In yet another aspect, an absorbent article has an absorbent material. The absorbent material has an outer surface. The absorbent article includes a temperature equilibrium agent. The temperature equilibrium agent substantially reduces the rate at which the absorbent article raises above equilibrium in an ambient environment.

BRIEF DESCRIPTION OF THE DRAWINGS

FIG. 3A illustrates toxin level as a function of temperature.

DETAILED DESCRIPTION OF THE INVENTION

Figure 1:
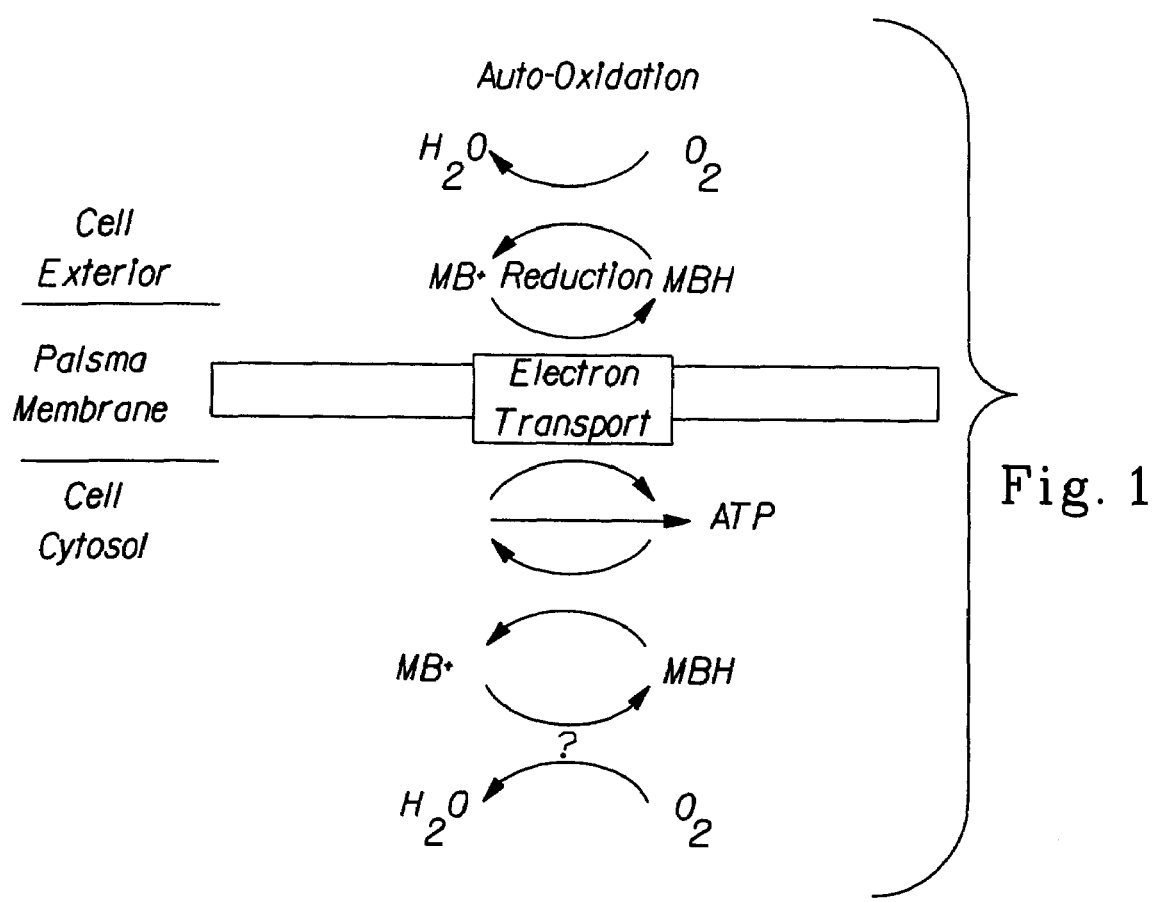
FIG. 1 illustrates the mechanism for ATP production within a cell.

The physiological/microbial activity occurring in the tampon during menstrual wear indicates a possibility that if the toxin producing strain of *S. aureus* is present it may produce toxin within or near the surface of the tampon. Moreover, the toxin initiates disease by coming into contact with and penetrating the vaginal mucosa. The risk of TSS can be reduced by 1) preventing *S. aureus* from colonizing the tampon; 2) altering the conditions within the tampon to insure that the perceived required conditions for toxin production are not present; 3) disrupting the epithelial or antigen presenting cell and T-cell binding sites for the toxin; 4) and/or retaining the toxin within the tampon.

Section A will provide terms which will assist the reader in best understanding the features of the invention and not to introduce limitations in the terms not consistent with the context in which they are used in this specification. Theses definitions are not intended to be limiting.

There are three phases to prevent a diseased state. Section B will discuss Phase I which involves the decrease in and/or prevention of surface or internal bacterial colonization of the tampon. Section C will discuss Phase II which addresses potential toxin production by the TSST-1 producing strain of *S. aureus* and therefore attempt to inhibit production of toxin within and/or on the surface of the tampon. Section D will discuss Phase III in which the goal is to deactivate the binding site of the toxin and/or prevent the toxin from coming into contact with the vaginal mucosa when the tampon is colonized by the TSST-1 producing strain of *S. aureus* and it is exposed to the required conditions for toxin production.

A. Terms

In general in this specification, the term "tampon" is used to refer to a finished tampon typically after a compression process and to any type of absorbent structure that is inserted into the vaginal canal or other body cavities for the absorption of fluid therefrom.

As used herein the terms "vaginal cavity," "within the vagina," and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein.

As used herein, the term "bound" means less than about 10% of the biological activity associated with inhibiting toxin production or growth of *S. aureus* in the tampon is lost by soaking the tampon over an 8 hour period at 100° F. in three times the syngnya capacity of sterile physiologic saline solution. The saline is removed from the tampon by compressing the tampon at 1 psi on a series of blotter paper until ≦0.5 grams of fluid is absorbed by the blotter paper on the last compression/absorption sequence and remeasuring the biological activity remaining in the tampon. The extraction and testing should be conducted in the absence of light. The ratio of initial biological activity of the tampon pre-extraction to post extraction is >90%.

As used herein, the term "partially bound" means less than about 50% of the biological activity associated with inhibiting toxin production or growth of *S. aureus* in the tampon is lost by soaking the tampon over an 8 hour period at 100° F. in three times the syngnya capacity of sterile physiologic saline solution. The saline is removed from the tampon by compressing the tampon at 1 psi on a series of blotter paper until $\leq 0.5$ grams of fluid is absorbed by the blotter paper on the last compression/absorption sequence and remeasuring the biological activity remaining in the tampon. The extraction and testing should be conducted in the absence of light. The ratio of initial biological activity of the tampon pre-extraction to post extraction is >50%.

As used herein, the term "substantially bound" means less than about 25% of the biological activity associated with the toxin production organic growth associated with *S. aureus* of the tampon is lost by soaking the tampon over an 8 hour period at 100° F. in three times the syngnya capacity of sterile physiologic saline solution. The saline is removed from the tampon by compressing the tampon at 1 psi on a series of blotter paper until $\leq 0.5$ grams of fluid is absorbed by the blotter paper on the last compression/absorption sequence and remeasuring the biological activity remaining in the tampon. The extraction and testing should be conducted in the absence of light. The ratio of initial biological extraction to post extraction is >75%.

As used herein, the term "biological activity" of a tampon is measured by the method described by J. Parsonnet, et. al. (J. Infect. Dis. 1996, 173: 98-103).

As used herein, the term "encapsulation" means the surrounding off or "caging" of a compound using a physical or chemical component.

As used herein, the term "nonabsorbent" means a non-absorbing component of an absorbent article, as distinct from the absorbing article itself, and that individual component (particle or fiber) will not swell or absorb fluid. Typically, this means less than a 15% weight gain of the component when placed in a saline solution for 10 minutes and then removed and compressed at 1 psi repeatedly against a series of blotter papers until less than about 0.5 gram of saline is absorbed by the blotter paper on the last compression/absorption sequence. As used herein an absorbent material, as distinct from an absorbent component is a material from which the absorbent core is made and may hold fluid in the intercapillary fibers or voids and may itself be an absorbent or non-absorbent component.

As used herein, the term "inhibitor" means any agent that prevents the normal growth of an organism or the activity of an enzyme or protein.

As used herein, the term "pre-toxin limiting agent" means any agent that prevents the initiation or actual production of a toxin.

As used herein, the term "deactivation" means to make less toxic or nontoxic.

As used herein, the term "permeable structure" means any article that selectively allows components of a particular size less than or equal to the particular size to readily pass through without substantial resistance. An overwrap is an example of a permeable structure.

B. Phase I: Reduce and/or Prevent Colonization of the Tampon by Vaginal Microorganisms To reduce the risk of TSS, antimicrobial agents are incorporated within an absorptive product such as a tampon to prevent the colonization of the tampon by bacterial species. If the bacterial species colonize, the bacteria can create toxin. If *S. aureus* is present and the toxin is created, the woman is at risk for TSS. The tampon represents a new ecological niche within the vaginal environment for the indigenous bacterial species of the vagina to colonize. New understandings of this indigenous population point toward the hypothesis that the greatest diversity, especially of minor species, in the vaginal biofilm/colony occurs at the surface of the vaginal mucosa. The highest probability of *S. aureus* initial colonization occurs at this vaginal mucosa surface/tampon interface. Components secreted by other species of vaginal bacteria can amplify toxin production by *S. aureus*. Therefore, to reduce the risk of an increase in population of *S. aureus*, via growth in the tampon, and extracellular components secreted by other organisms from affecting the potential rate of toxin produced, the present invention incorporates inhibitors that inhibit colonization into the tampon's design and construction. Section i. discusses the incorporation of antimicrobial agents into the absorptive product. Section ii. discusses the incorporation of antifouling agents into the absorptive product. Section iii. discusses the incorporation of biostatic agents into the absorptive product. Section iv. discusses the incorporation of negatively charged molecules. Finally, Section v. discusses the encapsulation of antimicrobial agents and biostatic agents.

i. Antimicrobial Agents

Antimicrobial agents may be incorporated into the construction of the absorptive, non-absorptive, and/or overwrap components of the tampon. Antimicrobial agents are agents which inhibit growth or kill bacteria. Controlling the localization of these antimicrobial agents is important. If the localization of the antimicrobial agents is not controlled, disruption and/or depletion of the indigenous microflora covering the vaginal mucosa would potentially be harmful to the overall health of the vaginal canal. The antimicrobial activities of many antimicrobial agents are dependent upon solubilization and uptake by the microorganisms of interest.

The antimicrobial agents may be covalently linked to the non-absorbent material of the tampon, either directly or through modification. The presence and detection of the antimicrobial agents by the vaginal microorganisms would be sufficient to delay or decrease the potential overall colonization of the tampon during typical wear. Modification of the antimicrobial agent to allow the antimicrobial to be immobilized, for example via $—CH_2—$ or $—CH_2—CH_2—$ etc. linker, while not obstructing their active sites would allow for increased availability and effectiveness against colonization of the tampon. However, linking the anitmicrobial agents to the absorbent component of the tampon may decrease the tampon's overall effectiveness.

Antimicrobial agents that can be utilized for this purpose may include but are not limited to Clindamycin, Lysostaphin, PHMB, Triclosan, and quaternary ammonia compounds. Clindamycin and Lysostaphin are discussed in more detail below.

An additional benefit of using Clindamycin is that this agent depresses toxin production by *S. aureus*. Clindamycin hydrochloride, or CLEOCIN® HCl, is currently used to treat vaginal infections. It is a semisynthetic antibiotic produced by 7(S)-chloro-substitution of the 7(R)-hydroxyl group of the parent compound lincomycin. Clindamycin inhibits bacterial protein synthesis at the level of the bacterial ribosome. It binds preferentially to the 50S ribosomal subunit and affects the process of peptide chain initiation. Although clindamycin phosphate is inactive in vitro, rapid in vivo hydrolysis converts this compound to the antibacterially active form. Clindamycin has been shown to be an effective antimicrobial agent for a number of organisms reported to be associated with bacterial vaginosis, such as *Bacteroides* spp., *Prevotella* spp., *Gardnerella vaginalis*, *Mycoplasma hominis* and *Peptostreptococcus* spp.

The antimicrobial agent lysostaphin (a zinc dependent, 25-kDa glycyl-glycine endopeptidase isolated from *S. simulans*) is a specific peptidoglycan hydrolase ("PGH") enzyme for *Staphylococcus* bacteria. PGH enzymes are incorporated and coordinated with the use of absorbent articles to reduce the risk of colonization of the absorbent article by *Staphylococcus*. PGH enzymes are naturally present in small amounts in bacteria where they are essential for cell wall re-modeling that must occur with cell growth and division. Because bacterial peptidoglycan structures differ significantly, PGHs can be found to target specific bacterial species or groups of related organisms. Specifically, the action of lysostaphin is hydrolysis of the —Gly+Gly— bond in the pentaglycine inter-peptide link joining Staphylococcal cell wall peptidoglycans, thereby, digesting the peptidoglycan "structural barrier" of the bacterial cell walls. Added in excess they rapidly digest peptidoglycan resulting in cell rupture. Therefore, lysostaphin, which is a specific PGH enzyme to Staphylococcal organisms, would prevent *S. aureus* and other Staphylococcal organisms from colonizing the tampon without adversely affecting the non-Staphylococcal dominate species of the vaginal canal. Lysostaphin's N-terminal of the enzymatic protein is the enzymatically active region and the C-terminal is what confers target cell specificity and allows it to distinguish between *S. aureus* and its parent cells *S. simulans* (Baba & Schneewind, EMBO J. 1996). Crosslinking the protein to a matrix via its C-terminal region would anchor the protein and still allow it to some degree to be enzymatically active against Staphylococcal spp.

ii. Antifouling Agents

Antibiofilm formation agents may be incorporated into an absorbent product such as a tampon to prevent the colonization of the absorbent product. Antifouling agents are an antibiofilm formation agent which may also be incorporated into the tampon's construction. The antifouling agents can be incorporated into the tampon's construction by binding. The binding of the antifouling agents is important because of the non impact or influence upon an environment external to its current environment. For example, an anti-microbial agent located in the tampon should not impact or influence the growth of bacteria outside the tampon.

The two types of antifouling agents which may be incorporated are Furanones and L-acyl homoserine lactones. Furanones are halogenated compounds that are known to depress gram-negative bacterial growth and kill gram-positive bacteria. L-acyl homoserine lactones are specific to gram-negative bacteria and are also known to control virulence factors. These agents need to be immobilized to the components of the tampon and prohibited from coming into direct contact with the microflora of the vaginal canal. Furthermore, quorum sensing signals are active biofilm forming signals for gram-positive organisms and may be employed to inhibit colonization of a tampon. Quorum signals will be discussed in depth in Section C of the Phase II discussions.

iii. Biostatic Agents

Biostatic agents decrease bacterial growth. Biostatic agents such as the common histochemical dyes, methylene blue, and gentian violet can be cross-linked to cellulose fibers and other potential absorptive materials. Methylene blue is a redox dye that raises the oxygen consumption of cells. This means that the protons (hydrogens) of the materials being oxidized are passed on to the oxygen molecules present in the environment. Methylene blue in an unbound state acts as an electron carrier short circuiting the electron transport process which is responsible for ATP (adenosine triphosphate) production within the cell (as shown in FIG. 1). A similar mechanism is hypothesized when methlene blue is bound to a fiber structure.

iv. Negatively Charged Molecules

Coating the absorbent article and its components with negatively charged molecules prevents the colonization of the absorbent product/tampon. Negatively charged tampon and/ or its components electrostatically repel bacterial cell surfaces which are negatively charged. If the materials of the absorbent product were negatively charged via the use of $PO_4$ or $SO_4$ etc., bacteria would be repelled from forming biofilm and or rapidly dividing in this negatively charged environment.

v. Encapsulation of Antimicrobial Agents and Biostatic Agents

Incorporating the encapsulation of enzymes and or active agents with an absorptive product such as a tampon prevents the colonization of *S. aureus*. Antimicrobial and/or biostatic agents can be encapsulated by the use of hydrophilic isocyanate polymers. These polymers are water-soluble and a variety of molecules can be incorporated into these hydrophilic urethane type polymers. During the polymerization of hydrophilic isocyanate prepolymers, carbon dioxide is typically generated keeping the oxygen levels in the immediate environment low. This low oxygen environment aides in the overall stability of any enzyme added to the prepolymer emulsion which becomes an integral part of the resultant copolymer. The enzyme(s) or other chemical antimicrobial/biostatic agent(s) participates in the polymerization and is typically chemically attached at multiple points within the resulting isocyanate copolymer matrix essentially becoming caged within the isocyanate polymer. As described previously, the overall availability and effectiveness of the caged enzyme may be increased by first modifying the attachment site of the enzyme to the polymer matrix via the addition of a "linker" molecule. Within this copolymer matrix a variety of enzymes have been shown to be thermally stable over time. Since this is an aqueous polymerization event, upon hydration of the copolymer matrix the enzyme or microbial agent becomes "active" and can exhibit a retention of specific activity as high as 80% of "uncaged" activity. This solubilization of the isocyante polymer allows for a controlled release of the enzyme as fluid triggers the solubilization of the urethane like gel. The components, which exhibit antimicrobial or biostatic activity, are covalently bound to the polymer. Upon hydration, the polymer is eroded to release the active material at the preferred site of action.

It is preferred to keep antimicrobial and biostatic agents isolated from the vaginal mucosa. This may be accomplished by the use of appropriate overwraps that cover the absorbent core. For example, formed film overwraps may be used or nonwoven overwraps made of rayon, cotton, polyesters, polyolefins that provide separation where the core is isolated from the surrounding vaginal tissue preventing destruction and/or alteration to the vaginal flora. The overwrap may also act in combination with the absorbent core to provide a one-way valve such that fluid enters the tampon and is irreversibly trapped. This tampon exhibits the one-way property when it is loaded with saline at 75% of syngyna capacity, allowed to equilibrate for fifteen minutes and then placed on blotter paper, the tampon is then rolled over the blotter paper without pressure applied to remove free fluid on the surface of the tampon. The tampon is then placed on a fresh blotter paper and compressed with a force of 1 psi. If the squeeze out on the blotter paper is less than 0.1 grams the tampon is considered to be a one-way valve.

Physical separation of the inhibitor or antimicrobial agent can be demonstrated by adding sterile saline solution (at syngyna capacity) gently blot the surface to remove free fluid and place the tampon containing the inhibitor onto an agar place colonized with a lawn of *Lactobacillas*. If the *Lactobacillas* lawn is not disturbed/killed at the contact point between the tampon and the agar plate physical separation is demonstrated.

C. Phase II: Prevent Toxin from Being Produced by TSST-1 Producing

Extensive in vitro work describes the environmental and genetic conditions required for *S. aureus* to produce TSST-1 toxin. Current in vivo physiological understanding of the dynamics of dissolved oxygen and carbon dioxide in the tampon during menstrual wear indicate that optimum conditions for toxin production by *S. aureus* must exist within the tampon. The oxygen required for potential toxin production within the tampon is believed to come from the inherent air within the tampon and the oxygen carried by the menstrual fluid absorbed by the tampon. The inherent oxygen of the tampon is essentially unutilized by the facultative microorganisms of the vaginal canal in the absence of blood/menses. However, in the presence of a heavy loading of blood/menses virtually all of the oxygen in the tampon can be consumed, while the dissolved carbon dioxide levels within the tampon rise significantly above that present in the vaginal environment.

Figure 2A:
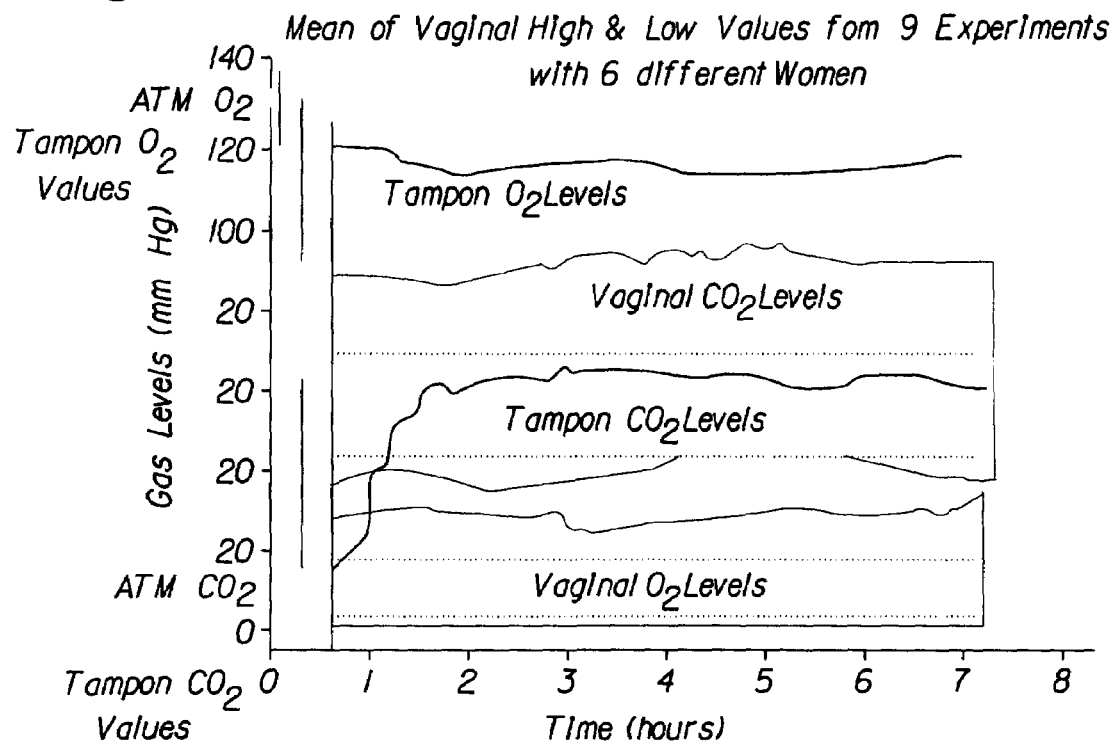
FIG. 2A illustrates gas level as a function of time for non-menstrual conditions.

As shown in FIG. 2A, during non-menstrual wear, carbon dioxide levels of the tampon rose to be essentially equivalent to those observed in the vagina. However, as shown in FIG. 2A, the oxygen levels within a non-menstrual tampon remained essentially at atmospheric levels.

Figure 2B:
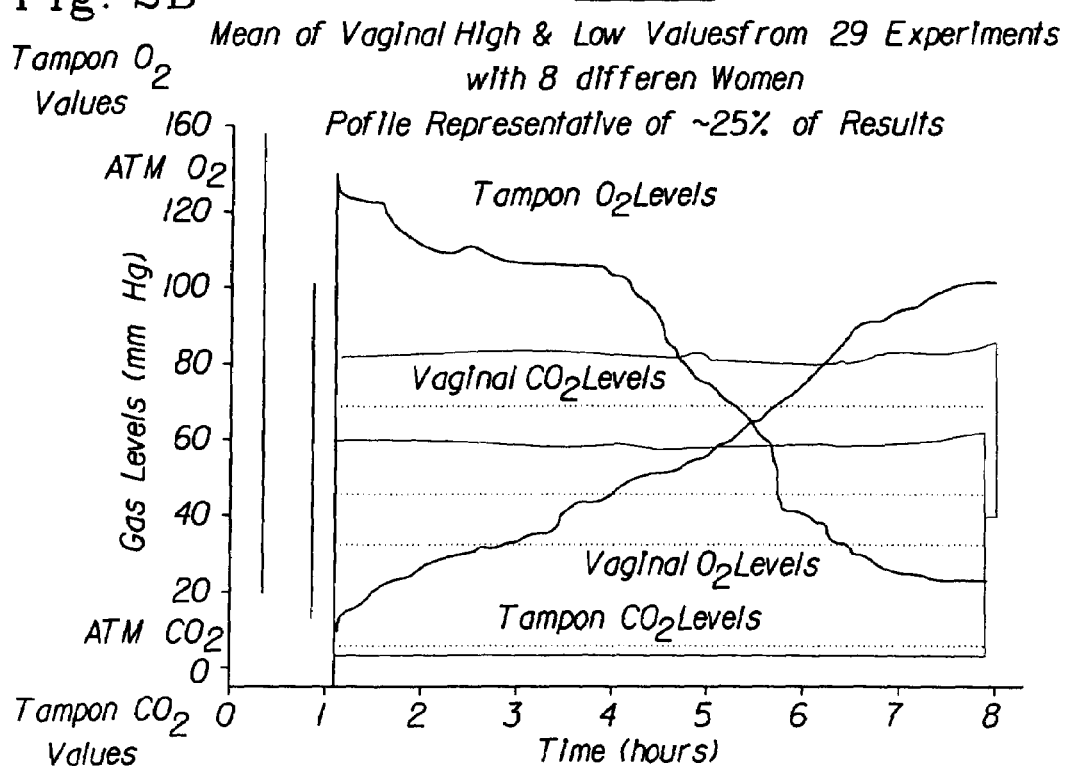
FIG. 2B illustrates gas level as a function of time for menstrual conditions.

As shown in FIG. 2B, during menstruation, the mean levels of carbon dioxide in about 50% of the tampons exceed the carbon dioxide levels of the vaginal environment. The mean levels of oxygen within the tampon decrease with apparent loading of the menses such that about 50% of the menstrual tampons reached an oxygen level near the ranges of oxygen levels observed in the vagina after 8 hours of wear. The decline of oxygen and the increase of carbon dioxide within a menstrual tampon may be at least partially related to microbial metabolic activity. Since menses is a mixture of venous and arterial blood, some of the oxygen may be "lost" due to partitioning from the gas phase to the liquid phase where it binds to un-oxygenated heme molecules present in the menses. The oxygen and carbon dioxide levels observed in a menstrual tampon after prolonged wear are consistent with in vitro data showing high levels of toxin production by *S. aureus* under similar $O_2/CO_2$ conditions.

Phase II provides several approaches to prevent toxin from being produced by the TSST-1 producing strains of *S. aureus*. Particularly, pre-toxin limiting agents are used to retard the production of bacteria produced toxins. Part i. discusses oxygen scavengers incorporated into the construction of the tampon. Part ii. discusses the alteration of the heme in menses. Part iii. discusses the encapsulation of antimicrobial agents via hydrophilic isocyanate polymers. Part iv. discusses the construction and/or additive to an absorbent structure, which either moderates (i.e. reduces) the thermal energy released during expansion of a tampon and/or cools the absorbent article. Part v. discusses the blockage of either the production of the octapeptide (Quorum Signal) or the binding of the peptide to the cell membrane receptor.

i. Oxygen Scavengers

In a number of in vitro experiments, oxygen has been shown to be essential for toxin production by *S. aureus*. An oxygen scavenger incorporated into the construction of a tampon would significantly reduce, if not entirely prohibit, toxin production within the product. Examples of oxygen scavengers, which could be employed, are antioxidants such as ascorbic acid, tocopherol and retinal. Compounds such as the antioxidants used in food substances such as butylated hydroxyanisole, di-tertiary-butyl-patacresol, propyl gallate, phenylenethiourea, and aldoalpha-napthylamine could also be used. Other oxygen scavenging agents employed may be composed of transition metal complexes, chelates of a salicyclic acid, salicylate salt, metal complex, and/or chelate of an organic polycarboxylic acid preferably an amino polycarboxylic acid wherein the transition metal could be supplied via the iron present in menses from the degraded heme molecules present in this body fluid. This type of oxygen scavenging molecule is typically activated by contact with water or water vapor.

These same oxygen-scavenging agents have the additional benefit of moderating the pH of the tampon. Because optimum toxin production occurs at a neutral pH, any agent which will lower the pH of the internal environment of the tampon into the acidic range could effectively reduce toxin production. Such agents are organic acids, for example ascorbic acid, polycarboxylic acid, etc. Not only does ascorbic acid act as a means to lower the pH and/or scavenge oxygen, but the ascorbic acid also deactivates the toxin. While the mechanism of deactivation is unknown, the present application includes the use of ascorbic acid in a tampon to deactivate the potential presence of TSST-1 toxin to the point of rendering it non-toxic, i.e. not lethal in animal experiments.

ii. Alteration of the Heme in Menses

Another approach is to alter the heme in menses such that it has a lower affinity for oxygen. This may be accomplished by placing BPG (2,3-bisphosphoglycerate) within the tampon. BPG lowers the affinity of oxygen for hemoglobin by a factor of 26. This is the compound used to dissociate oxygen from the heme enabling the unloading of oxygen to tissue capillaries in the body. If the oxygen can not associate with heme, it is probable that it will no longer be bioavailable to the microorganisms potentially colonizing the tampon such as *S. aureus* and therefore, avoid the perceived required conditions for toxin production within the tampon during menstruation.

iii. Encapsulation of Antimicrobial Agents via Hydrophilic Isocyanate Polymers

In Phase I, there was a discussion of encapsulation of antimicrobial agents via hydrophilic isocyanate polymers to prevent colonization of the tampon. This same technology can be utilized to encapsulate agents which would prevent or decease the production of toxin by *S. aureus*. An alternative method to the isocyanate polymer encapsulation would be the use of alginates precipitated from solution. Material that may be physically encapsulated includes but is not limited to carbon black, antimicrobials, oxygen scavengers (i.e. ascorbic acid), quorum signal analogs and/or blockers, methylene blue, chitosan malate, etc. These same compounds can be added to absorbent foams either pre- or post-polymerization. Other agents which can be added include but are not limited to ascorbic acid, tocopherol, glycerol, etc., all of which have been shown to reduce toxin production and/or deactivate the toxin TSST-1. Algenic acid can also be made into fibers via reaction with cellulosic fibers and provides a matrix for the additional cross-linking of a number of compounds such as chitosan malate, which is known to depress microbial growth of *S. aureus* and significantly reduce its ability to produce the TSST-1 toxin. Thus, alginate particles/fibers act as an active agent carrier that can be used with or in a component of the construction of an absorbent article such as a tampon to depress microbial growth of *S. aureus* and significantly reduce its ability to produce the TSST-1.

iv. Construction and/or Additive to an Absorbent Structure which Either Moderates or Reduces the Thermal Energy Released during Expansion of a Tampon and/or Cools the Absorbent Article A potential risk factor for toxin production in vivo is believed to be elevated temperature. In an attempt to moderate or depress any tendency the tampon may have to exist at an elevated temperature in vivo, a number of compounds could be used. As shown in FIG. 3A, in in vitro experiments a one degree Fahrenheit increase in temperature can result in a 50% increase in TSST-1 production by *S. aureus*.

This patent application claims any technique of construction and/or additive to an absorbent structure, which either moderates (i.e. reduces) the thermal energy released during expansion of a tampon and/or cools the absorbent article (either of compressed or non-compressed construction) such that it preferably remains at or below typical body temperature of 98.6° F. If the internal tampon temperature does rise above the ambient body temperature of 98.6° F., it returns to 98.6° F. within 30 minutes.

A number of currently marketed products are tested for their potential change in internal temperatures upon hydration, i.e. a measure of their absorbent material's heat of dissolution. The experimental design involves the use of non-lubricated condoms submerged with the open end above water into a 98.6° F. water bath. A thermocouple is placed in a small hole drilled through the middle of a tampon, which is inserted into the condom such that it too is submerged into the water bath. A second thermocouple is placed between the tampon and the surrounding condom. The condom-surrounded tampon is then allowed to come to the temperature of 98.6° F. Sterile saline is also allowed to come to a temperature of 98.6° F. in the same water bath. A gush of the 98.6° F. sterile saline (at syngyna capacity) is then pumped in such that the tampon becomes saturated. The internal and external tampon temperature is monitored. In addition to commercially available products, a tampon constructed of a super absorbent material as well as one constructed of foam absorbent material (FAM) is tested.

Figure 3B:
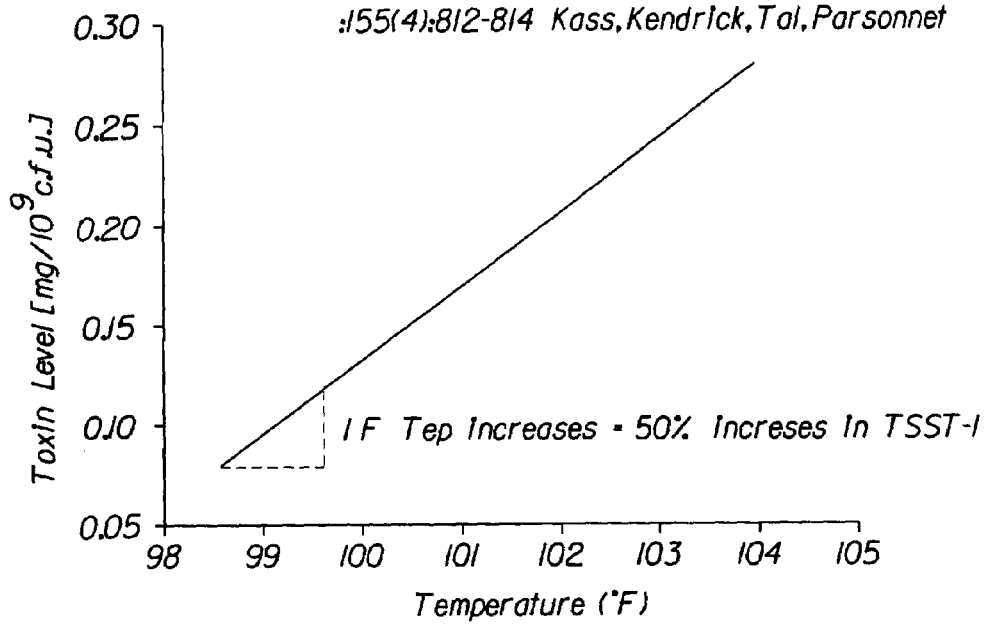
FIG. 3B illustrates temperature as a function of time for a tampon.
Figure 3B:
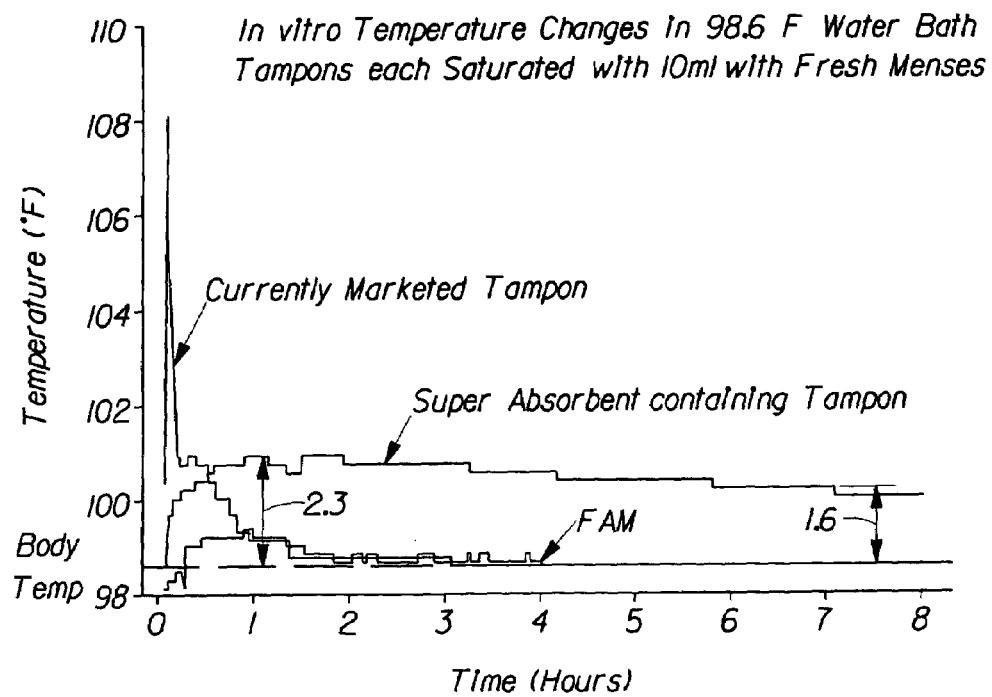

As shown in FIG. 3B, no changes were observed for the tampons "external" temperature.

As shown in FIG. 3B, currently marketed products that are constructed as a compressed "plug" of absorbent material exhibited a sharp rise in internal temperature upon hydration with fresh menses. The thermal energy is a result of the release of expansion energy upon hydration of the compressed absorbent plug structure. Referring to FIG. 3B, note that the temperature of the commercially available products quickly returned to water bath temperature after the action of hydration. The tampon composed of super absorbent material exhibited an internal temperature of over 2° F. above that of the water bath and sustained this temperature for a prolonged period of time of 7 hours. Temperature increase of the super absorbent tampon may be related to the heat of dissolution of the materials used in its construction, a phenomena previously not considered in tampon construction. The foam absorbent material ("FAM") constructed tampon's internal temperature rose only slightly and quickly returned to the original ambient temperature of 98.6° F.

The Epson Salt or magnesium sulfate hepta-hydrate ($MgSO_4$—$H_2O$) is somewhat endothermic in nature and could be employed to counteract any physical reactions to elevate temperature within the tampon. Epsom Salt or magnesium sulfate hepta-hydrate ($MgSO_4$—$H_2O$) has a low energy of dissolution. Certain absorbent materials such as psyllium husk and certain FAMs have been shown to moderate the temperature of a tampon under the experimental conditions outlined above such that the temperature of the tampon is not significantly elevated (as shown in FIG. 3A and FIG. 3B). Other agents that possess zero or less than zero heats of dissolution include but are not limited to NaCl, $Ca(NO_3)_2$—$4H_2O$, $Na_2CO_3$—$10H_2O$, $CaCl_2$—$6H_2O$ and various other magnesium salts.

An absorbent foam such as FAM or another absorbent may be saturated with a solution of salt such as CaCl2, MgCl2, or sodium ascorbate or absorbic acid and then dried leaving a residual salt or acid content within the foam. It has been found that concentrations of these materials on a weight percent of foam between 0.1% and 10% can inhibit TSS-1 production. The architecture of the tampon being either a compressed plug or a loose sack has been demonstrated to impact the internal temperature of the tampon upon hydration. The loose sack design moderates the temperature of the tampon such that its internal environment does not exceed the temperature of the body during absorption of bodily fluids. In this design cellulose could also be employed in the construction of the product to act to establish a less dense product to allow for better temperature control, i.e. body temperature or less.

V. Blockage of Either the Production of the Octapeptide (Quorum Signal) or the Binding of the Peptide to the Cell Membrane Receptor This patent application claims the use of such signals and/or signal analogs/antagonist, either natural or artificial in origin to repress the signal for the ultimate production of TSST-1 by *S. aureus* in an absorbent article and or menstrual cup, diaphragm or other like devices. Likewise any agent that can either prevent the production of the octapeptide, bind up the octapeptide after its production such that it is no longer available to "feed back" to the cell or occupy the binding sites on the cell membrane such that the cyclic peptide—signaling molecule octapeptide (agr D/autinducing peptide) can not bind and signal for toxin production in the absorbent articles.

Figure 4:
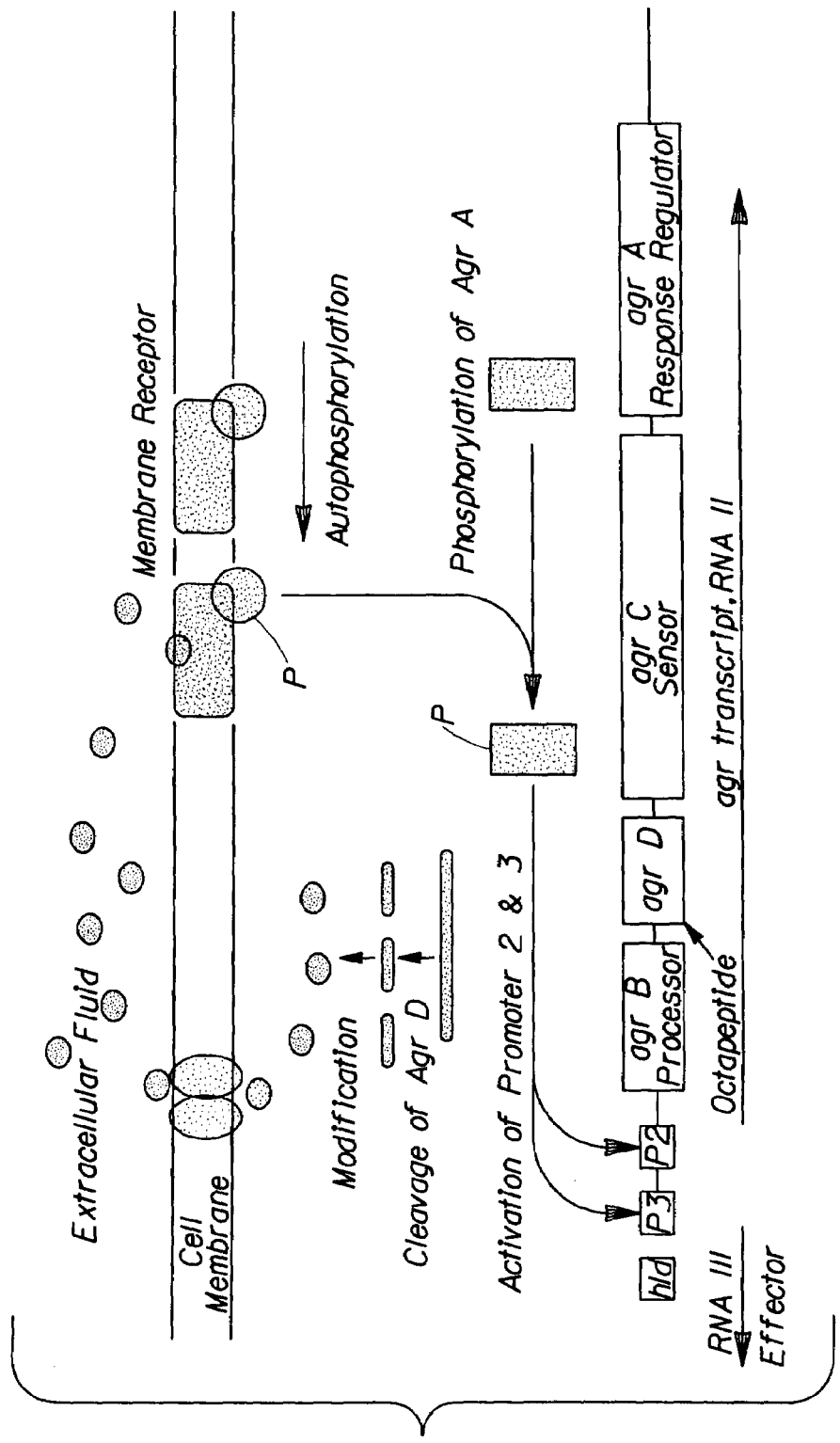
FIG. 4 illustrates the production of the octapeptide, its release into the environment and its signaling for the production of the toxin.

The gene cluster or operon that regulates the expressions of the toxin designated TSST-1 is an example of Quorum Sensing. When an infectious agent such as *S. aureus* invades a host, it first attaches and attempts to grow and form a biofilm. The agr system controls the production of many secreted proteins: positively regulating enterotoxins, epidermolytic toxins and enzymes produced by staphylococci, and negatively controls such proteins such as Protein A, fibronectin-binding protein and coagulase. During this time signals are sent out into the immediate environment where the biofilm is forming. When enough of this signal is present, it binds to a membrane receptor on the *S. aureus* cells to indicate that a critical density of bacteria has been reached and cells of *S. aureus* may be released into the environment to continue the process of infection. Therefore, when the population of the cells is dense enough and the concentration of signal is high enough such that an individual bacterial cell can detect the signal toxin synthesis is initiated. This high level of signal is referred to, as a "Quorum" of signal, the signal compound in the case of TSST-1 is an octapeptide auto inducing peptide. Toxin production occurs due to a cascade of phosphorylation events in response to the quorum signal within the cell that brings about the activation of the promoter region, which controls the expression of the genes encoded for the toxin. After the biofilm "burst", the *S. aureus* cells adhere to a new site within the host and the "Quorum Sensing" process begins again. FIG. 4 depicts the production of the octapeptide, its release into the environment and its signaling for the production of the toxin. (Arvidson, S. *European Conference on Toxic Shock*, September 1997)

As shown in FIG. 4, blockage of either the production of the octapeptide auto inducing peptide (Quorum Signal) or the binding of the peptide to the cell membrane receptor, could essentially lock the door to toxin production. With the use of natural repressors for TSST-1 production such as competing analogs or antagonists peptides. Therefore, this patent application claims the application of such an analog or antagonist peptide/compound to the construction of and/or as an additive to an absorbent article such as a tampon to reduce the expression of TSST-1 toxin by *S. aureus* during the absorbent articles use.

D. Phase III: Disrupt Toxin Binding Sites and/or Prevent Toxin from Contacting Vaginal Mucosa Phase III of this patent application claims any technique (i.e. application of technique to an absorbent article) or tampon construction that acts to retain/adsorb the toxin into/on the tampon preventing the toxin and/or toxin producing strains of *S. aureus* from coming into contact with the vaginal mucosa. To prevent any TSST-1 toxin production from contacting the vaginal mucosa, the tampon will be designed to specifically attract and bind TSST-1 toxin from and within the tampon from the immediate environment around the tampon or from blood/menses entering the tampon.

Several ways have been developed to retain the toxin in the tampon by a variety of ligand binding sites. The binding of the specific toxins onto the fiber surfaces of the tampon prevents them from contacting vaginal mucosal tissue, and thereby, is expected to provide some degree of protection to the wearer against the toxin. The toxin can be retained by a direct affinity to its own antibody or antibody fragment or a chemical hapten resembling its own binding site. Specific polypeptides or fragments of polypeptides which show an affinity for the toxin can also be employed to directly link the toxin. Toxins may also adhere to specific oligonucleotide sequences which create direct or combinatorial libraries and screen them for binding activity to the toxin that can identify these oligonucleotides. Indirectly the toxin can be linked by saturating the environment with protein A.

There are a variety of methods to attach ligands to fibers and/or materials, such as: 1) solid matrix support though cellulosic fibers: 2) activation coupling chemistry with the use of sodium periodate: 3) site directed antibody coupling though carbohydrates: 4) coupling of antibody fragments with sulfhydral residues: and 5) amplification of antibody binding sites such as avidin coupled matrixes or biotinylated antibodies or fragments.

The above-described ligands need not only be linked to the tampon's absorptive fibers/particles and/or overwrap and/or materials (i.e. psyllium, FAM, etc.). The toxin binding ligands may also be attached to non-absorptive/or absorptive glass beads, zeolites and charcoal as examples. In addition, the ligands may be attached to the inner surface of the tampon overwrap composed of formed film topsheet, 3-D films, high loft structures, low capillary force gradients (hollow fibers, etc.). These materials act not only as one-way flow valves, allowing flow into the tampon but not out, but also as the final "net" to catch the toxin before coming into contact with the vaginal mucosa.

In order for the toxin to remain in the tampon once it becomes linked to a particular ligand, the ligand must be anchored to the particular absorbent or non-absorbent material composing the tampon. If the biologically active molecules is not bound or partially bound to the internal matrix of the tampon there may be a risk of the toxin coming into contact with the vaginal mucosa. Here again, the one-way flow valve overwrap structure can be incorporated to the final "safety net" to catch any toxin or toxin complex from coming into contact with the vaginal mucosa.

Overwraps that isolate or trap fluid in the tampon by providing a physical separation between the fluid in the core and the top surface of the tampon or vaginal membrane are defined as "one way valves."

All documents cited in the Detailed Description of the Invention are, in relevant part, incorporated herein by reference; the citation of any document is not construed as an admission that it is prior art with respect to the present invention While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising an absorbent material, said absorbent material comprising a biostatic agent and an inhibitor, wherein said biostatic agent is at least partially bound to the absorbent material and substantially inhibits the growth of bacteria within the absorbent article and wherein said inhibitor is at least partially bound to the absorbent material and substantially inhibits the growth of bacteria within the absorbent article.

2. The absorbent article of claim 1, wherein said biostatic agent is a histochemical dye.

3. The absorbent article of claim 1, wherein said biostatic agent is methylene blue.

4. The absorbent article of claim 1, wherein said biostatic agent is gentian violet.

5. The absorbent article of claim 1, wherein said biostatic agent is cross-linked to cellulose fibers.

6. The absorbent article of claim 5, wherein said biostatic agent is a histochemical dye.

7. The absorbent article of claim 5, wherein said biostatic agent is methylene blue.

8. The absorbent article of claim 5, wherein said biostatic agent is gentian violet.

9. The absorbent article of claim 1, wherein said absorbent article is a tampon.

10. The absorbent article of claim 1, wherein said inhibitor is an antimicrobial agent.

11. The absorbent article of claim 1, wherein said inhibitor is an antifouling agent.

12. The absorbent article of claim 1, wherein said inhibitor is confined in an unbound state within said absorbent article by a permeable structure which encases the absorbent material, said permeable structure being configured to allow body fluids to flow through said permeable structure in a first direction and substantially prevent flow of the inhibitor from passing back through said permeable structure and thereby exiting said absorbent article.

13. The absorbent article of claim 11 wherein said antifouling agent is a quorum sensing compound.

14. The absorbent article of claim 13, wherein said quorum sensing compound is a peptide.

15. The absorbent article of claim 13, wherein said quorum sensing compound is an octapeptide.

16. The absorbent article of claim 13, wherein said quorum sensing compound is a cyclic peptide.

17. The absorbent article of claim 13, wherein said quorum sensing compound is dlautoinducing peptide.

18. The absorbent article of claim 1, wherein said absorbent material further comprises an antifouling agent.

19. The absorbent article of claim 18, wherein said absorbent article is a tampon.

* * * * *

UNITED STATES PATENT AND TRADEMARK OFFICE
CERTIFICATE OF CORRECTION

PATENT NO.        : 7,402,722 B2                                        Page 1 of 1
APPLICATION NO.   : 11/725462
DATED             : July 22, 2008
INVENTOR(S)       : Donna Rene Hill et al.

It is certified that error appears in the above-identified patent and that said Letters Patent is hereby corrected as shown below:

In the Drawing
Figure 3A, after 50%, delete "increses" and insert --increases--.

Column 14
Line 58, delete "dlautoinducing" and insert --d/autoinducing--.

Signed and Sealed this

Twenty-fourth Day of March, 2009

JOHN DOLL
*Acting Director of the United States Patent and Trademark Office*